United States Patent [19]

French

[11] Patent Number: 5,099,702
[45] Date of Patent: * Mar. 31, 1992

[54] PERIMETER MOUNTED POLYMERIC PIEZOELECTRIC TRANSDUCER PAD

[75] Inventor: Barry J. French, Bay Village, Ohio

[73] Assignee: French Sportech Corp., Bay Village, Ohio

[*] Notice: The portion of the term of this patent subsequent to Nov. 28, 2006 has been disclaimed.

[21] Appl. No.: 380,157

[22] Filed: Jul. 14, 1989

Related U.S. Application Data

[63] Continuation-in-part of Ser. No. 292,317, Dec. 30, 1988, abandoned, which is a continuation-in-part of Ser. No. 226,616, Aug. 1, 1988, abandoned, which is a continuation-in-part of Ser. No. 182,913, Apr. 18, 1988, Pat. No. 4,883,271, and a continuation-in-part of Ser. No. 785,969, Oct. 10, 1985, Pat. No. 4,761,005, and a continuation-in-part of Ser. No. 904,356, Sep. 8, 1986, Pat. No. 4,824,107.

[51] Int. Cl.⁵ .................................................. G01L 1/16
[52] U.S. Cl. ........................ 73/862.68; 128/671; 128/721; 128/782; 310/338; 273/454
[58] Field of Search ............... 128/671, 721, 774, 681; 73/862.68, DIG. 4, 379; 310/338, 800; 273/1 GC, 1 E, 1 ES, 1 F, 184 R, 186 A, 181 G, 181 J, 181 K, 57.3, 454, 460

[56] References Cited

U.S. PATENT DOCUMENTS

| | | | |
|---|---|---|---|
| Re. 32,180 | 6/1986 | Lewiner et al. | 128/721 |
| 3,124,132 | 3/1964 | Sullivan et al. | 128/675 |
| 3,210,993 | 10/1965 | Shoor et al. | 73/862.64 |
| 3,836,900 | 9/1974 | Mansfield | 128/721 |
| 4,023,054 | 5/1977 | Taylor | 73/774 |
| 4,216,403 | 8/1980 | Krempl et al. | 310/800 |
| 4,304,126 | 12/1981 | Yelke | 310/800 |
| 4,509,527 | 4/1985 | Fraden | 128/721 |
| 4,534,557 | 8/1985 | Bigelow et al. | 272/76 |
| 4,691,556 | 9/1987 | Mellander et al. | 73/12 |
| 4,757,453 | 7/1988 | Nasiff | 128/782 |
| 4,883,271 | 11/1989 | French | 273/1 GC |

FOREIGN PATENT DOCUMENTS 1273135  5/1972  United Kingdom ............... 310/339

*Primary Examiner*—Kyle L. Howell
*Assistant Examiner*—Kennedy J. Schaetzle
*Attorney, Agent, or Firm*—Peter D. Sachtjen

[57] ABSTRACT

A force pad is provided with a flexible polymeric piezoelectric transducer strip mounted on the perimeter of a resilient support pad for measuring force and change in force in industrial, medical and sports applications.

16 Claims, 6 Drawing Sheets

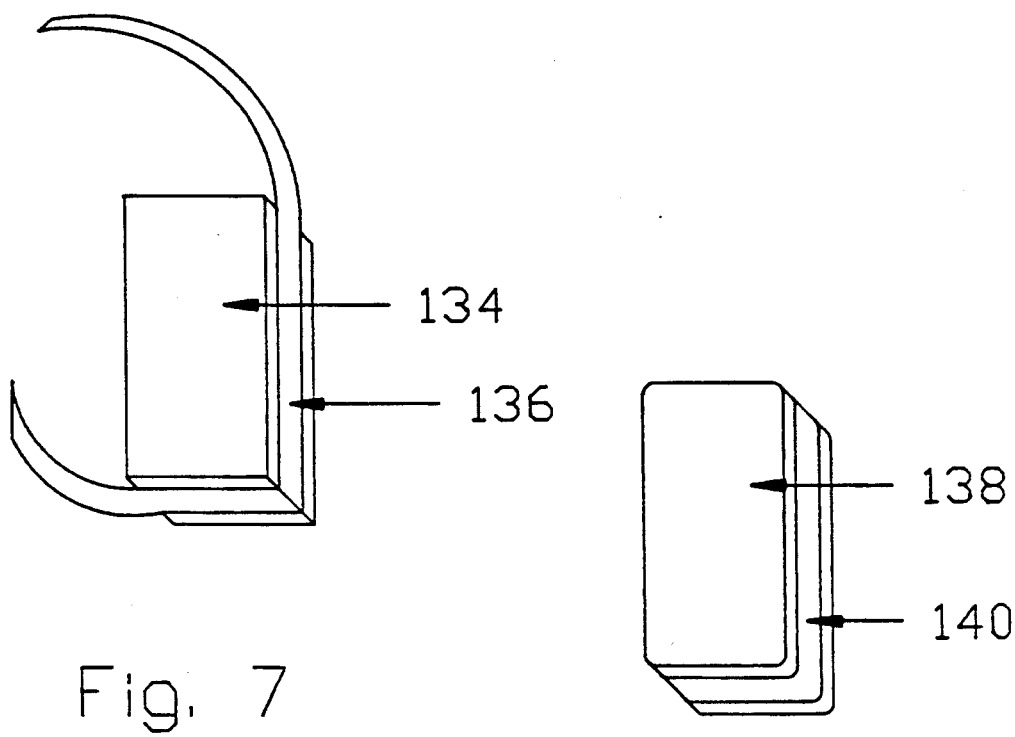
Fig. 7
Fig. 8
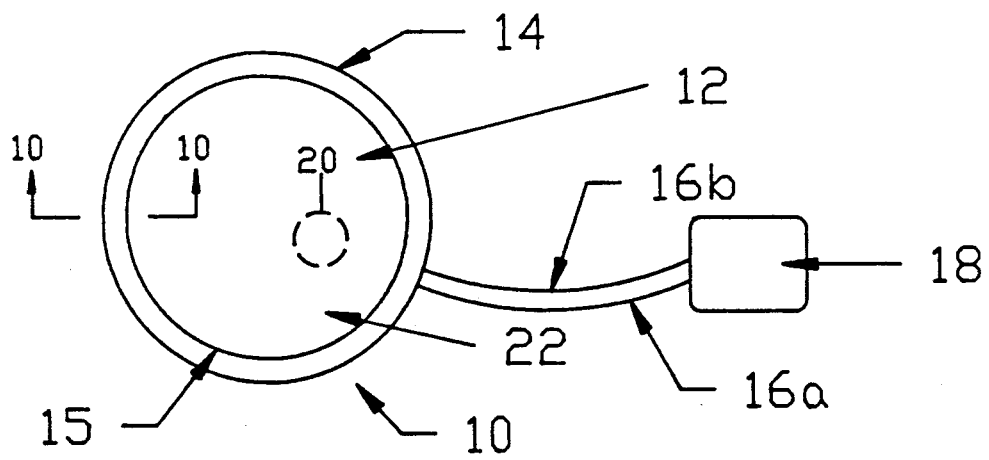
Fig. 9

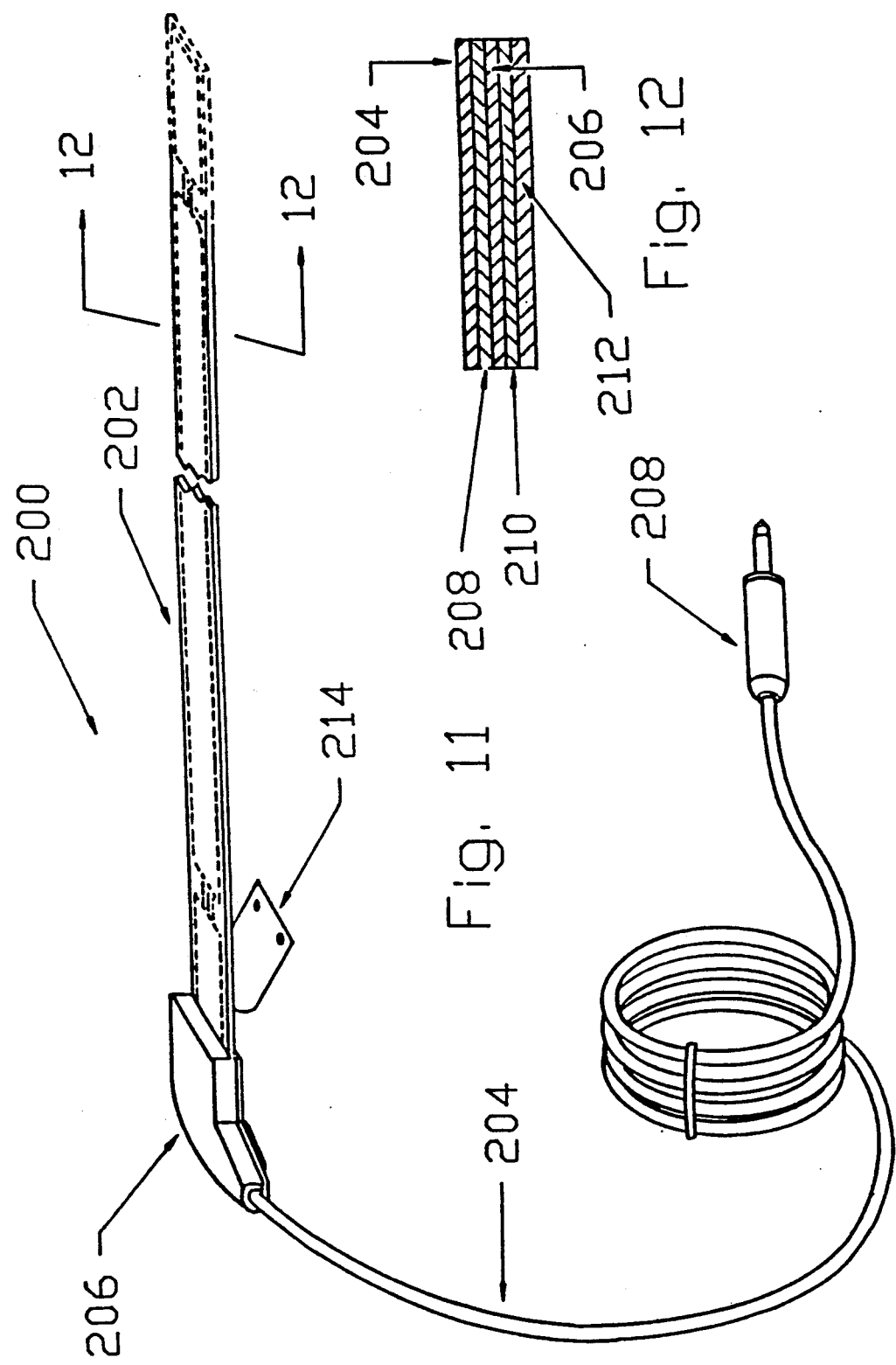

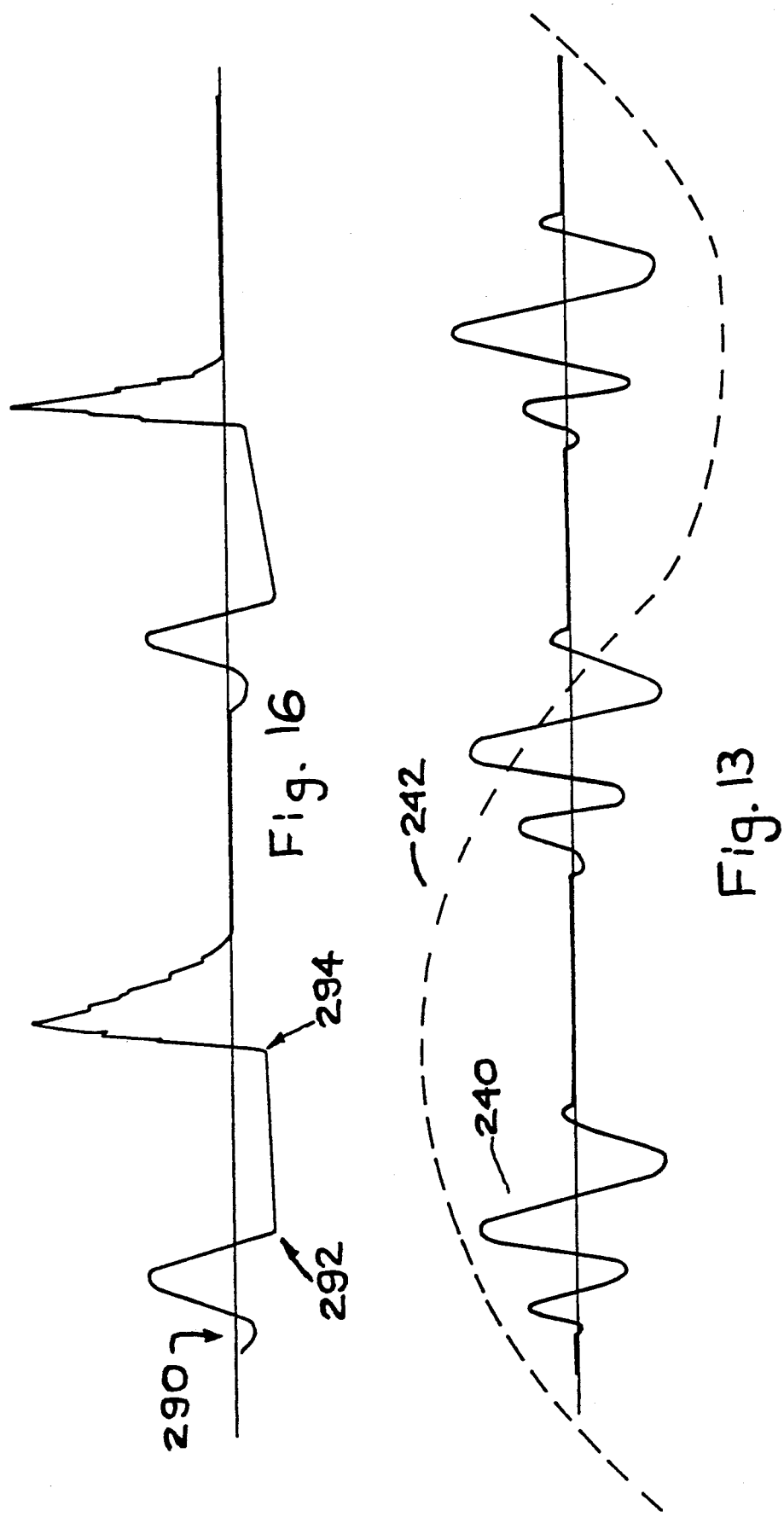

PERIMETER MOUNTED POLYMERIC PIEZOELECTRIC TRANSDUCER PAD

CROSS REFERENCE TO RELATED APPLICATIONS

This application is a continuation in part of U.S. patent application Ser. No. 292,317 filed on Dec. 30, 1988, now abandoned, which is a continuation in part of U.S. patent application Ser. No. 226,616 filed on Aug. 1, 1988, now abandoned which is a continuation-in-part of U.S. patent application Ser. No. 182,913 filed Apr. 18, 1988 and issued as U.S. Pat. No. 4,883,271, and a continuation in part of U.S. patent application Ser. No. 785,969 filed Oct. 10, 1985 and issued as U.S. Pat. No. 4,761,005, and also a continuation-in-part of U.S. patent application Ser. No. 904,356 filed Sept. 8, 1986 and issued as U.S. Pat. No. 4,824,107.

TECHNICAL FIELD

This invention relates to electromechanical transducers for measuring the magnitude of forces and for detecting changes in force, and, in particular, to polymeric piezoelectric transducer devices providing output information with regard to force, frequency, velocity, energy, work and power of objects in contact with or impinging upon the transducer device. The invention finds use in sports, medical and industrial applications.

BACKGROUND ART

Various devices are employed for detecting force or change in force and other characteristics related thereto. Exemplary of the range of such devices are force platforms in the biomedical, sports and industrial fields measuring large scale ground reaction forces, and seismographic mattresses in the medical fields detecting small scale cardiovascular and respiratory forces.

Force platforms, in particular, measure ground reaction forces in biomedical applications such as gait analysis, analysis of sway patterns in neurology, evaluation of sports performance, assessment of the degree of rehabilitation and numerous other medical, sports and industrial applications. These platforms typically use multiple strain gauges, capacitive sensors or load cells for sensing force and changes in force. Due in part to the inherent size limitations of the sensors, they cannot directly act as the load receiving surface and must be used in arrays and coupled to a platform surface, generally a rigid, light and very stiff planar member. One sensor for such force platforms is disclosed in U.S. Pat. No. 3,210,993 wherein a ceramic piezoelectric transducer encircles a solid metal cylindrical support column. The transducer is stressed in accordance with the radial expansion of the column caused by applied loading to the platform to generate a signal in accordance therewith. To achieve uniformity across the platform surface, complex circuitry is required to interpret the multiple sensor signals generated at each column.

For applications such as seismographic mattresses, rigid supporting surfaces are, of course, not practical. More resilient, compliant materials are required for patient comfort and to provide an accommodating surface which allows for intimate coupling between the patient and the transducer device. Seismographic mattresses are useful for monitoring patients' heart and respiration rates. These mattresses are non-invasive transducers for measuring these biological signals, thereby eliminating the need for restricting and psychologically intimidating sensor attachment to the patient. Typically a sheet of transducer material is placed under the mattress to measure these minute biological forces. The sensor material may be piezoelectric or capacitive film or the like. Various systems using such materials have been proposed for monitoring patient movement and functions such as respiratory and cardiovascular activity. One typical approach to patient monitoring is disclosed in U.S. Pat. No. 4,320,766 wherein a medical apparatus for the monitoring of patient activity on a bed comprises a flexible capacitive motion sensor placed under the patient mattress. The sensor uses an active layer, underlying the entire bottom surface of the mattress. The sensor consists of two courses of dielectric material placed in contact with one another. Movements of the patient on top of the mattress cause the courses to move relative to one another, thereby generating an electric charge in the active layer. The electrical charge is detected by a pair of metallized plastic sheets which form a capacitive antenna. The resultant system is a sandwich of five discrete, mattress size layers all of which are shielded in a metallized plastic film bag. Another patient monitoring device is disclosed in U.S. Pat. No. 4,438,771 wherein a pair of conductive layers connected to a monitoring circuit are spaced by an insulating layer, the layers being substantially coextensive with the bottom surface of the patient mattress. A further approach is disclosed in U.S. Pat. No. 4,509,527 wherein a transducer sheet underlying the patient mattress comprises a piezoelectric sheet engaged on either side between a pair of plastic sheets having interengaging convex surfaces. Patient movement flexes the piezoelectric sheet at the convex surfaces to generate an output signal proportional to the magnitude of the changing mechanical forces which induce the electrical charges. Each of the foregoing patient monitoring devices requires a plurality of operative layers of generally expensive material, typically as much as 20 square feet for adult sized mattresses. Further, the monitoring sensor is normally located under the mattress resulting in significant attenuation of the already minute biological signals to be detected. Also, the mounting of the sensor under constantly flexing loading conditions can accelerate aging wear of the sensor materials due to abrasion.

In view of the foregoing limitations of force measuring devices, it would be desirable to provide a force platform which produces uniformity and repeatability of force measurement, and changes therein, over the entire supporting surface. In other words, each time an identical event occurs, regardless of the point of loading, the output information should be the same. Further, it would be desirable to provide a force platform operable over a wide range of forces. Moreover, such devices should be rugged and durable, able to withstand the forces encountered in operation without damage to the sensors. Furthermore, the the amount of sensor material required to measure large sensing areas should be reduced.

BRIEF SUMMARY OF THE INVENTION

The present invention achieves these desired features and overcomes the above limitations and disadvantages of prior force platforms by providing a detecting device which is durable, inexpensive, and mechanically simple for measuring, with sensitivity and uniformity over a broad dynamic range, and displaying parameters relating to movement on a loading surface. The invention provides a detecting device which may be subjected to randomly located loadings and will uniformly supply an output related to various parameters thereof. More particularly, a detecting device for detecting changes in loading in accordance with the invention comprises a load receiving member of a homogeneous material having a first or front face for experiencing the loading, a second face in opposed relation to said first face, and side wall means interconnecting said first face and said second face. A flexible polymeric piezoelectric transducer strip is disposed in stress receiving relationship with substantially the entire periphery of the side wall. The piezoelectric transducer strip is stressed in accordance with changes in said loading and yields an electrical output signal in accordance with said changes and characteristics of changes in the loading of the load receiving member.

More particularly, the load receiving member may be a polymeric pad of circular, rectangular, oval or like rounded configuration. Examples of suitable materials are natural and synthetic rubber, plastics, polymeric foams, and in general resilient materials which are locally deformable and substantially uniform in elastic constant. A matching of the material and the application is important. For instance, materials with higher elastic constants yield lower voltages and higher frequency waveforms. Such materials when coupled with a perimeter mounted polymer piezoelectric transducer strip are useful in detecting and measuring higher loading changes, such as randomly located, high mass impacts. The lower elastic constant materials yield higher voltage signals and lower frequency waveforms. These materials are useful in detecting and measuring lower level loading changes, such as seismographic mattresses and patient monitors.

It appears that impacts on a pad cause the generation of force waves outwardly and substantially evenly, and the measurement of the force waves by the piezoelectric means will measure the force, the frequency and the energy value of the force waves.

The elastic compliance of the polymeric piezoelectric film that engages the periphery of the pad is many times that of piezoceramic materials. This enables good coupling of the sensor to the resilient support pad without disturbing the mechanical motion of the pad. The low mechanical and acoustic impedance of the polymeric piezoelectric film compared to piezoceramics provides efficient energy transfer to the sensor. The efficiency can be further improved by using a polymer adhesive to mount the sensor that has similar impedance values as the polymeric piezoelectric film. Additionally, inasmuch as piezoelectric materials are anisotropic in nature, in that their electrical and mechanical responses differ depending upon the axis of applied mechanical strain or stress, orientation of the sensor in relationship to the machine or stretch direction can contribute to maximum generation of charge for a given applied force. The invention orients the film so that forces acting on the load-receiving face cause an applied tensile stress in the direction of stretch, thereby accentuating the resulting charge produced for a given force. In comparison, sheet devices, for a given force acting on the face, cause a compressive stress that results in significantly lower charge generation.

BRIEF DESCRIPTION OF THE DRAWINGS

The above and other advantages of the present invention will become apparent upon reading the following detailed description of the preferred embodiments taken in conjunction with the accompanying drawings in which:

FIG. 7 is a rectangular force pad with a piezoelectric means being applied to the perimeter thereof;

FIG. 8 is a rectangular force pad with rounded corners, and a piezoelectric sensor applied to the perimeter thereof;

FIG. 9 is a plan view of a circular force pad having a polymeric piezoelectric transducer strip applied to the perimeter thereof;

FIG. 11 is a perspective view of a flexible polymeric piezoelectric transducer strip in accordance with the present invention;

FIG. 12 is an enlarged cross sectional view taken along line 12—12 of FIG. 11;

FIG. 13 is a typical biological function wave form for a person lying on a force pad in accordance with the present invention;

FIG. 16 is a typical wave form for a person jumping on the force pad of FIG. 15.

DETAILED DESCRIPTION OF THE PREFERRED EMBODIMENTS

Figure 10:
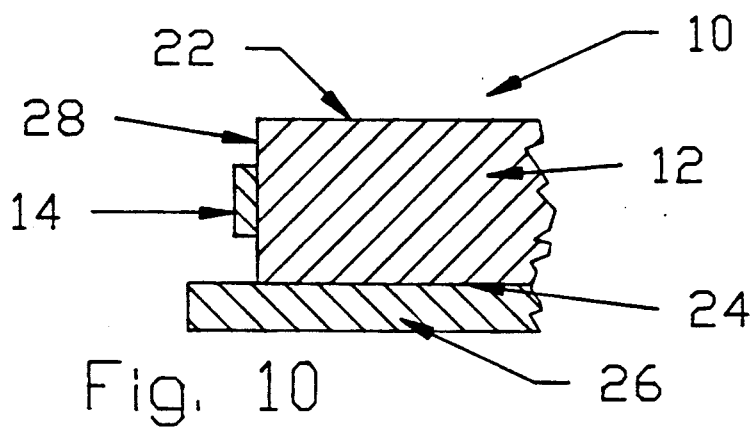
FIG. 10 is an enlarged fragmentary cross sectional view taken along line 10—10 in FIG. 9.

Referring to the drawings for the purpose of describing the preferred embodiments only, FIGS. 9 and 10 show a perimeter mounted polymeric piezoelectric film transducer pad 10 comprising a circular cylindrical force pad 12 having a flexible polymeric piezoelectric transducer strip 14 mechanically coupled to the side wall 15 of the pad 12. The strip has output leads 16a and 16b operatively connected to an output device 18. As described in greater detail below, the force pad 10 measures, accurately and uniformly, loading changes caused by movement of an object 20, illustrated in dashed lines, randomly impacting or moving on a portion of the front surface 22 of the force pad 12 as detected by the strip 14 and output by the device 18. The rear or bottom surface 24 of the force pad 10 is carried by a support member 26.

Pads, i.e. support structures generally defined by parallel top and bottom surfaces circumscribed by a peripheral side wall, are particularly good means for measuring the characteristics of impacts when the piezoelectric sensor means are used. It has been found that the piezoelectric means, preferably of the flexible polymeric piezoelectric film strip, can be used very advantageously with many different types of force pads. It is believed that impacts rendered on a force pad generate force waves which emanate substantially regularly throughout the pad, and that their measurement can yield the characteristics of the impact. The piezoelectric means can be permanently or removably affixed to the perimeter of the force pad.

The type and orientation of force pad depends on the use to which it will be put. For measuring projectiles such as a baseball, tennis ball, or volleyball, or other projected objects, a foam or rubber force pad could be oriented vertically. For use in sports applications, a horizontal force pad made out of a hard rubber or resilient foam on which the person could jump or the like would be appropriate. To measure the force of someone hitting the pad, a foam pad could be mounted vertically to receive the person's fist, foot or body impacts. The leads and indicator devices are not shown in FIGS. 1-4 for sake of clarity, but may be of the type discussed previously.

Figure 1:
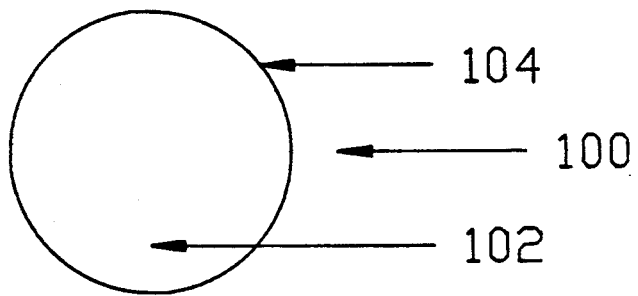
FIG. 1 is a top view of the force pad of circular construction according to the invention.
Figure 2:
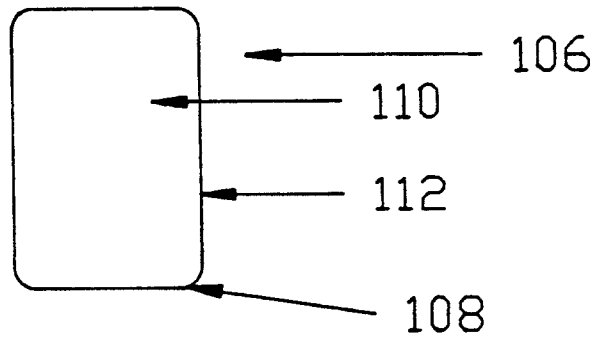
FIG. 2 is a front view of a rectangular force pad according to the invention.
Figure 3:
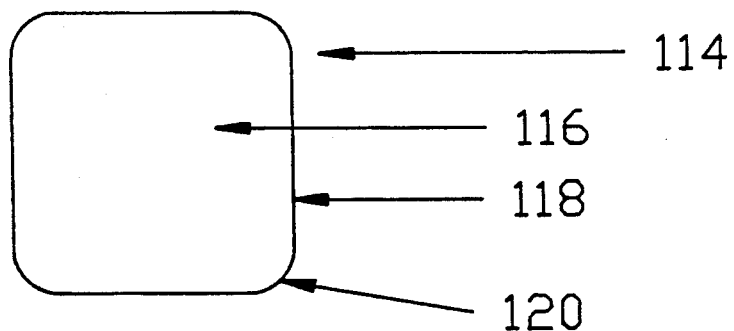
FIG. 3 is a front view of a square force pad with rounded corners according to the invention.

FIG. 1 shows a vertical force pad assembly 100 having a pad 102 and a piezoelectric assembly 104 as described above attached thereto. When assembly 100 is made out of foam, rubber, or the like and suspended vertically, it could be used to measure baseballs pitched at it. The piezoelectric device 104 could be an integral part of force pad 102, and the circumference could be 35 inches or larger.

Figure 4:
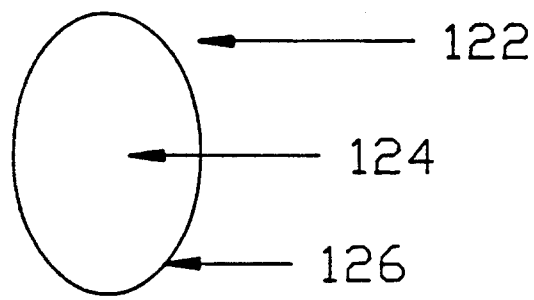
FIG. 4 is an irregular shaped force pad with piezoelectric sensor means applied to the perimeter thereof.

FIG. 4 shows another force pad assembly 122 having a force pad 124 having an irregular shape, around which is attached a flexible piezoelectric transducer 126. If device 122 were made out of plastic or other foam and if large enough, it could be used for a blocking dummy for football players or a target for martial arts fighters. Soft force pads, yielding low frequencies but high voltages for impacts which they receive, are less resilient and more comfortable to engage.

The foregoing devices have been discussed as being used in sports training applications, but there are many other uses as well. In sporting events, they would find many uses. Likewise, they could be used in biomedical applications, industrial applications and the like. In nearly every instance, the piezoelectric sensor is not touched by the article being measured.

Figure 5:
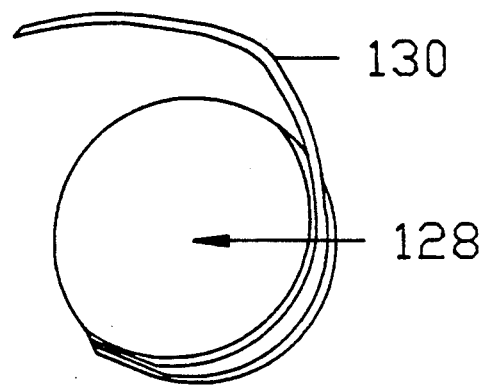
FIG. 5 is a perspective view of a piezoelectric means incorporated in a strap being applied to a round force pad.
Figure 6:
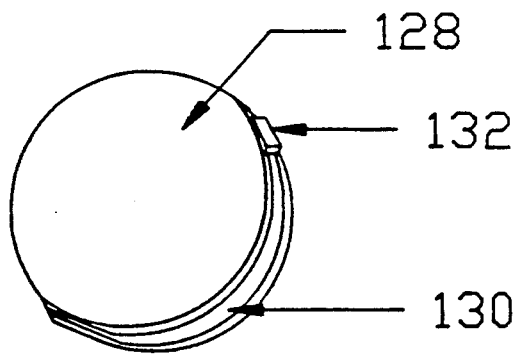
FIG. 6 is a perspective view of a round force pad with a strap applied to the perimeter thereof.

The piezoelectric film may be incorporated in a strap rather than being an inherent part of the force pad. Thus, referring to FIG. 5, a force pad 128 has a piezoelectric film strip 130 being applied to it. The film strip 130 is as described above but with perhaps a thicker Mylar coating, and its end has a Velcro patch or glue type adhesive for slightly overlapping the other end of the strap to yield a lapped or overlapped strap when connected. FIG. 6 shows a force pad 128 with the strap firmly in place. FIG. 7 shows a rectangular force pad 134 with a piezoelectric film strip 136 about to be adhered to its perimeter, while FIG. 8 shows a rectangular force pad 138 having rounded corners with its strip 140 in place.

The piezoelectric material referred to with respect to the various embodiments described herein is preferably a polarized polyvinylidene fluoride (PVDF) film sandwiched between metallized layers of electrically conductive metal. This is the same material described in co-pending U.S. patent application Ser. No. 785,969 filed Oct. 10, 1985 and issued as U.S. Pat. No. 4,761,005, and also a continuation-in-part of U.S. patent application Ser. No. 904,356 filed Sept. 8, 1986, and issued as U.S. Pat. No. 4,824,107, incorporated herein by reference. This multilayered material is marketed under the trademark KYNAR by the Pennwalt Corporation, 900 First Avenue, King of Prussia, Pa. Thus as shown in FIG. 11, the piezoelectric assembly 200 comprises an elongate transducer strip 202 electrically coupled to a cable 204 at a connector housing 206. The cable 204 terminates with a molded connector plug 208 adapted to be connected to the output device 18, referenced above. As shown in FIG. 12, the transducer strip 202 is a multilayer laminate comprising an outer Mylar layer 204, a middle polymeric piezoelectric sheet 206 having metallized coatings 208 and 210 on either side thereof, and an inner Mylar layer 212. The layers 212 and 204 are adhesively attached to the sheet 206. Additionally, the inner layer may be provided with an adhesive layer for coupling attachment to the pad, with the adhesive protected prior to installation by peel back release paper 214. As used in the embodiments described herein, the piezoelectric film is approximately 28 microns in thickness, and the oppose metallized layers are silver of about 0.1 microns in thickness.

More particularly, the force pad 12 in FIG. 9 is formed of a homogeneous material of substantially uniform elastic constant. While the force pad may be formed of high elastic constant materials such as metals, woods, and hard plastics, it is generally preferred to use polymeric materials, such as rubber, softer plastics, polymer foams and like materials having an elastic constant similar to the film strip and that are resilient and locally deformable to aid in wave energy propagation to the transducer strip 14.

The force pad 10 may be mounted, horizontally, vertically or inclined on a base member 26. Preferably, the pad 12 is cylindrically shaped defined by the front load receiving surface 22, a parallel spaced rear support surface 26, and bounded by a continuous side wall 28. While illustrated as circular, other cylindrical shapes (rectangular, rectangular with rounded corners, oval and the like) can be used for accurately and uniformly measuring changes in loading on any portion of the front surface 22. Moreover the side wall may be truncated, although such shape increases the difficulty of achieving continuous mechanical coupling of the strip 14 to the side wall.

Referring to FIGS. 9 and 10, the transducer strip 14 is coupled to the side wall 28, mechanically, compressively or adhesively. Excellent coupling has been obtained through adhesive attachment using pressure sensitive adhesive supplied by 3M, such as Product No. Y-9485 for the polymeric foam pad, and Product No. 950 for solid rubber pads. The strip 14 so coupled has material properties well matched to the pad 14 and provides high piezoelectric sensitivity, low mechanical and acoustic impedance to produce accurate, ascertainable outputs to the device 18 throughout a broad range of loadings. As opposed to other piezoelectric materials such as quartz, Rochellesalt, PZT and BaTiO3 piezoelectric materials, the flexible polymeric piezoelectric strip 14 provides many times the voltage output for a given force, enabling the sensing of movements as low as respiration and pulse. Moreover, because of the toughness and flexibility of the materials, the strip 14 is not subject to breakage or loss of dipolar properties when subjected to mechanical impact in velocity measuring embodiments described below.

As will become hereinafter apparent, the strip 14 may be located at various positions on the side wall. For the monitoring of respiration and pulse requiring sensing of low force changes, a location adjacent the top surface has been found most satisfactory. For large, heavy objects impacting the load receiving surface, location of the transducer strip 14 adjacent to the rear surface is preferred. Notwithstanding the foregoing, generally accurate output may be obtained without location dependency with the strip 14 located in intermediate positions along the side wall.

To provide accurate output of changes in loading at random locations on portions of the front surface, i.e. no location dependency, it is important that the strip 14 operatively engage substantially the entire periphery of the side wall. Gaps in such peripheral engagement result in outputs for identical loadings which vary from location to location. This is exemplified in Example 1 below.

EXAMPLE 1

A 1 inch thick vinyl nitrile foam pad, RUBATEX 338V, was equipped with a flexible polymeric piezoelectric transducer strip continuously about the side wall of the force pad (Pad 1). An eight pound shotput was dropped on the front surface from a distance of 16 inches at five locations, the center and four equally circumferentially spaced locations about two thirds radius from the center. The above pad was then fitted with a strip covering three quadrants with a 90° gap in the northwest (NW) sector (Pad 2). An eight pound shotput was dropped on the front surface from a distance of 16 inches at five locations, the center and four equally circumferentially spaced locations about two thirds radius from the center. The outputs are set forth below.

| Location | Pad 1 | Pad 2 |
| --- | --- | --- |
| Center | 8.5 volts | 6.5 volts |
| East | 8.5 volts | 9.9 volts |
| South | 8.2 volts | 11.5 volts |
| West | 8.7 volts | 1.0 volts |
| North | 8.6 volts | 2.0 volts |

The uniformity provided by continuous perimeter mounting of the transducer strip as provided by Pad 1 is particularly important where uniformity and repeatability of information is desired, such as velocity targets and force platforms described below. Where detection of signal characteristics is desired, such as seismographic mattresses and patient monitors described below, the transducer strip should be mechanically coupled to the side wall along sufficient perimeter to output the selected characteristic with accuracy and distinction.

As mentioned above, the material selection for the pad to provide the mechanical coupling with the transducer is also important. Metals, ceramics, rigid plastics and like materials, under tests similar to the above, show high location dependency, random peak amplitudes in the wave form, and polarity reversal. Such irregularities are experienced on both hard and resilient base surfaces. Typical results for such rigid materials are set forth in Example 2 below.

EXAMPLE 2

A ½ inch by 12 inch circular polypropylene disk was equipped with a continuous flexible piezoelectric transducer strip and tested in accordance with the conditions of Example 1. In one condition, the disk was supported on a wood surface and in another condition the disk was supported on a 1 inch thick polymeric foam pad.

| Location | Wood Support | Foam Support |
| --- | --- | --- |
| Center | 1.8 v first peak | .1 v first peak |
|  |  | −.7 v second peak |
| East | .3 v first peak | .1 v first peak |
| South | .4 v first peak | .3 v first peak |
| West | .1 v first peak | −.2 v first peak |
| North | .2 v first peak | .3 v first peak |
|  |  | .9 v second peak |

Unlike the pads of the present invention wherein there is uniformity in the first peak signal, and substantially less significant second peak signals, the above were replete with numerous peak signals with very little damping of the signal until at least four peaks were determined on the wood surface, and two or more were determined on the foam support. It is thought that the wave propagation frequencies were so high and undampened that reverberations sensed throughout the sensor length interfered with a sensing of the prime impact signal.

Another important aspect for achieving uniformity of readings across the entire sensing area is the manner in which the pad assembly is mounted. The support member should not restrain the propagation of wave energy to the transducer strip. Mechanically or adhesively attaching the pad to the support member can create significant location dependencies, particularly in devices where the transducer strip is located adjacent to the support member such as in projectile measurement plates and ground reaction force plates. On the other hand, for measuring minute biological signals where it is preferred to locate the sensor adjacent to the supporting surface, only limited reduction in the quality of the output signal is observed.

Figure 14:
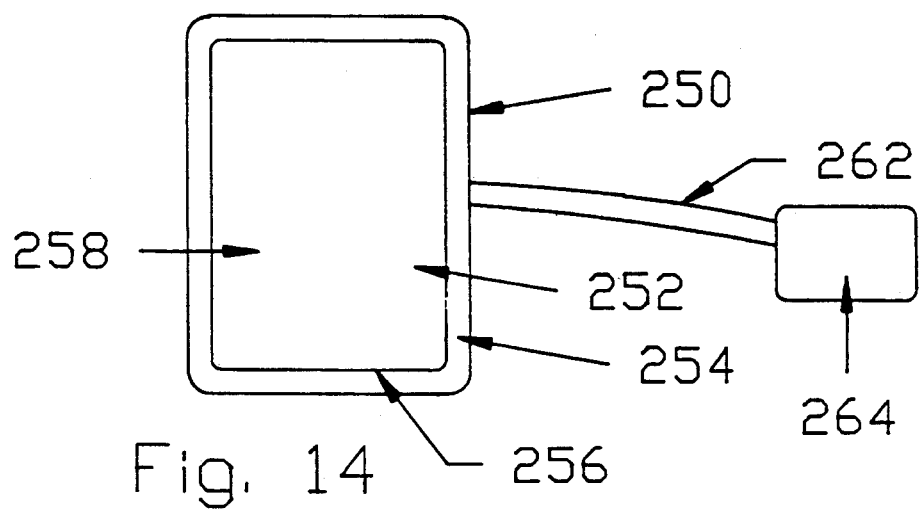
FIG. 14 is a plan view of a seismographic mattress in accordance with the present invention.

The force pad of the present invention provides extreme sensitivity to random loading on the top surface. For instance, on a 2 inch thick ethylene vinyl acetate (EVA) foam mattress having dimensions of 42 centimeters by 68 centimeters with generously radiused corners and ¼ inch wide transducer strip mounted within ⅛ inch of the top surface, a common marble dropped from 12 inches generated a peak output signal of 320 mv., merely blowing on the pad from 6 inches produced readily detectable 50 mv. peak output signals. Moreover, with a person lying on the pad, a ballistic cardiograph signal of 40–100 mv. was regularly periodically outputted with a rise and fall of the peak in accordance with respiration. A typical signal of a person at rest is shown in FIG. 13. Therein, the ballistic cardiograph pulse produces a periodic characteristic waveform 240, the amplitudes of which rise and fall along a periodically occurring respiration curve 242 shown in dashed lines. Such a device is well suited as a seismographic mattress or pad for patient monitoring of movement or cardiovascular and respiratory functions. Thus as shown in FIG. 14, a patient monitoring mattress 250 comprises a deformable, locally compressible pad 252 which has a flexible polymeric piezoelectric transducer strip 254 mechanically coupled to the side wall 256. The top surface 258 of the pad may directly support the patient without the need for a conventional mattress. The bottom surface 260 may be carried by conventional bedding support structure, or alternatively the pad 252 may be supported on a rigid base which in turn is carried by the bedding support structure. Leads 262 attached as described above to the transducer strip 254 are connected to a suitable output device 264 which may comprise an oscilloscope, strip chart recorder, alarm device or the like. Additionally the output signals may be processed by filtering or comparative techniques as described in U.S. Pat. Nos. 4,686,999 and 4,320,766 to enhance evaluation of the output signal. Furthermore, it has been demonstrated that the transducer pad as described above has such extreme sensitivity as to enable vocal sounds to be transmitted through the pad and received by the transducer strip, such that if the output device 264 additionally includes a speaker system of the proper type, patient speech is also provided as output. Because of the sensitivity of the present invention to changes in loading, the device described above is useful in many patient monitoring situations, in addition to those referenced above. The device can be used for remote monitoring of gross body movement of the patient, patient presence on the device so as to accommodate continuous information as to the patient's status.

The seismographic mattresses described above provide clear output signal with low background noise when the transducer strip is mechanically coupled about substantially the entire perimeter of the mattress. Thus in comparison with the prior art mattress systems using a sheet of piezoelectric film under the mattress where approximately 20 square feet of film may be required, the perimeter mount typically employs a ¼" wide band approximately 18 feet long so that only 54 square inches or approximately 0.38 square feet is needed. Compared with employing a sheet underlying the mattress, the present invention requires only approximately 2% of the film, or a savings of 98%. It has been determined that the transducer strip length can be reduced to provide further cost advantages. Moreover, a reduction in length does not diminish the signal to noise ratio. By way of example, an 81 inch by 33 inch EVA foam mattress 3 inches thick, as supplied by Rubatex Corporation as Product No. EVA R-5010, was equipped with a transducer strip adhesively mechanically coupled about the entire side wall perimeter. With a 200 pound man lying on the surface, heart pulse peaks with amplitudes of 130 mv were clearly noted with background noise of around 20 mv were noted. The transducer strip was progressively removed from the side wall of the mattress. At 80% coupling the peak heart pulse was similar. At 60% coupling the peak heart pulse was around 100 mv and the background noise was approximately 20 mv.

The present invention is also well suited as an accurate, sensitive device for measuring activities related to a standing body movement onto and from the platform. For instance, the vertical height of a jump (elevation of the center of gravity), the velocity at take off, the coupling time, i.e. the time between initial preparatory jumping movement and lift off, as well as peak or average power expended in jumping can be determined in accordance with conventional means associated with jump platforms.

Figure 15:
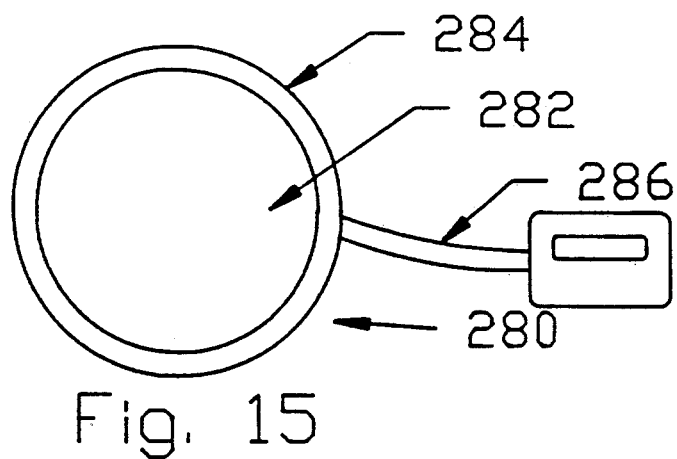
FIG. 15 is a plan view of a force pad coupled to an output device.

Referring to FIG. 15, there is shown a force platform 280 comprising a resilient polymeric pad 282 encircled by a polymeric flexible piezoelectric strip 284. The output leads 286 of the platform 280 are electrically connected to an analog/digital device for displaying the values for the various parameters. FIG. 16 shows a typical force curve generated by person on the platform during the course of a jump from and onto the pad. Therein, point 290 represents the time or start of the jumping activity, point 292 the time of take off and point 294 the time of landing. The time interval between points 290 and 292 represents the coupling time of the jump. It will be noted that the coupling time is represented by two distinct phases. First, an eccentric phase as the jumper is lowering the body center of mass preparatory to jumping and a concentric phase as power is expended in jumping followed by a decreasing force as the weight is removed from the platform terminating with a minimum force indicative of the take off. The time interval between take off and landing is the jump or air time and is one parameter for indicating vertical rise of the center of mass, or jump height. Alternatively the slope of the curve between points is a function of take off velocity from which vertical rise may also be determined. The power expended in the jump may also be derived as a function of body weight. Thus the force over the concentric phase or the force over the landing phase may be used as a function of body weight in power determination. For such devices, it is preferred to use a high durometer rubber pad for the platform which is resilient and locally deformable. Suitable examples of such material are 50 to 70 durometer synthetic rubber compounds.

A device of the type discussed above may also be used for determining the force of a single impact by an object on a portion of the front surface, for example the force and the speed of a sport object such as a baseball, soccer ball, volleyball or the like, as well as impacts or blows by sports participants. Therein, force may be obtained by detecting peak charge or by integrating the charge curve over the time interval between initial impact and start of rebound.

It has been observed that an application of a vinyl dip coating, or similar, to the force pad acts to improve the sensor's ability to accurately and reliably detect minute forces. This thin (approx. 5-15 mils), compliant membrane or laminar layer apparently facilitates the transmission of the shock waves generated from movement on the face of the force pad.

Various other embodiments and modifications of the above described embodiment will be apparent to those skilled in the art. Accordingly the scope of the invention is defined only by the accompanying claims.

What is claimed is:

1. A force measuring device for detecting force and changes in force comprising:
    a support formed of a resilient locally compressible material, said support being defined by a front surface for randomly receiving the force applied on discrete portions thereof, a rear surface in opposed relation to said front surface, and a peripheral side wall circumscribing and bounding said front surface and said rear surface, the area of said front surface having a substantially greater area than the area of said side wall;
    a flexible polymeric piezoelectric transducer coupled to said side wall, said transducer being stressed and yielding an electrical output signal in accordance with said force applied on said discrete portions.

2. A force measuring device as recited in claim 1 wherein said front surface is in opposed parallel relation to said rear surface.

3. A force measuring device as recited in claim 1 wherein said side wall is substantially cylindrical.

4. A force measuring device as recited in claim 3 wherein said side wall of said support defines a circular cylinder.

5. A force measuring device as recited in claim 1 wherein said transducer strip is disposed in stress receiving relationship with substantially the entire periphery of said side wall.

6. A force measuring device as recited in claim 5 wherein said transducer strip is located on said side wall intermediate said front surface and said rear surface.

7. A force measuring device as recited in claim 1 wherein said support is a homogeneous material having a substantially uniform elastic constant.

8. A force measuring device as recited in claim 7 wherein said material is a polymeric material having an elastic constant similar to said transducer strip.

9. A force measuring device as recited in claim 1 wherein indicating means are connected to said transducer strip for indicating at least one value of a characteristic of said electrical output signal.

10. A force measuring device as recited in claim 1 for indicating at least one value related to movement on the device wherein said front surface receives such movement and said front surface and said rear surface are bounded by a continuous cylindrical peripheral wall and said polymeric piezoelectric transducer is acoustically coupled and mechanically mounted to said side wall, said transducer providing an electrical signal in response to a change of said at least one value of a characteristic of said force.

11. A force measuring device as recited in claim 1 wherein said support is a high durometer elastomeric material.

12. A force measuring device as recited in claim 1 wherein said transducer is located on said side wall adjacent said rear surface.

13. A force measuring device as recited in claim 1 including means for removably securing said transducer to said side wall.

14. A force measuring device for indicating at least one value related to movement on the device comprising:
a support formed of a resilient locally compressible material, said support being defined by a front surface for randomly receiving the movement when applied on discrete portions thereof, a rear surface in opposed relation to said front surface, and a peripheral side wall transverse to said front surface and said rear surface, said side wall circumscribing and bounding said front surface and said rear surface, the area of said front surface having a substantially greater area than the area of said side wall;
a flexible polymeric piezoelectric transducer, means acoustically coupling and mechanically mounting said piezoelectric transducer to said side wall, said transducer providing an electrical signal in response to a change of said at least one value of a characteristic of said movement.

15. A detecting device for detecting and outputting randomly located loadings, comprising: a load receiving member formed of a homogeneous resilient material which is locally deformable and substantially uniform in elastic constant, said load receiving member being defined by a cylindrical side wall, a top wall and a bottom wall, said side wall having a substantially uniform height said top wall and said bottom wall being substantially parallel, said top wall receiving said randomly located loadings and having a substantially greater area than the area of said side wall; an elongated flexible polymeric piezoelectric transducer strip engaging substantially the entire perimeter of said side wall; and pressure sensitive adhesive means securing said transducer strip to said side wall, said transducer strip outputting an electrical signal upon and in accordance with said random loadings of said top wall.

16. The detecting device as recited in claim 15 wherein said homogeneous resilient material is selected from the group consisting of natural rubbers, synthetic rubber, plastics, and polymeric foams.

* * * * *